United States Patent
Adkesson et al.

(10) Patent No.: US 8,183,417 B2
(45) Date of Patent: *May 22, 2012

(54) PURIFICATION OF BIOLOGICALLY-PRODUCED 1,3-PROPANEDIOL

(75) Inventors: Dennis N. Adkesson, Decatur, IL (US);
Albert W. Alsop, Wilmington, DE (US);
Tyler T. Ames, Wilmington, DE (US);
Luis A. Chu, Landenberg, PA (US);
James M. Disney, Decatur, IL (US);
Bryan C. Dravis, Fishers, IN (US);
Patrick Fitzgibbon, Hockessin, DE (US); James M. Gaddy, Decatur, IL (US); F. Glenn Gallagher, Wilmington, DE (US); William F. Lehnhardt, Lovington, IL (US); Jefferson C. Lievense, Forsyth, IL (US); Michael L. Luyben, Perkiomenville, PA (US);
Mayis Seapan, Landenberg, PA (US);
Robert E. Trotter, Wilmington, DE (US); Gregory M. Wenndt, Lafayette, IN (US); Eugene K. Yu, Hockessin, DE (US)

(73) Assignees: E. I. du Pont de Nemours and Company, Wilmington, DE (US); Tate & Lyle Ingredients Americas LLC, Decatur, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/035,246

(22) Filed: Feb. 25, 2011

(65) Prior Publication Data

US 2011/0152583 A1 Jun. 23, 2011

Related U.S. Application Data

(62) Division of application No. 10/839,188, filed on May 5, 2004, now Pat. No. 7,919,658.

(60) Provisional application No. 60/468,231, filed on May 6, 2003.

(51) Int. Cl.
*C07C 29/74* (2006.01)
*C07C 31/18* (2006.01)

(52) U.S. Cl. ........................ 568/868; 568/872

(58) Field of Classification Search ............ None
See application file for complete search history.

(56) References Cited

U.S. PATENT DOCUMENTS

| | | | |
|---|---|---|---|
| 4,380,678 A | 4/1983 | Sirkar | |
| 5,034,134 A | 7/1991 | George et al. | |
| 5,194,159 A | 3/1993 | George et al. | |
| 5,334,778 A | 8/1994 | Haas et al. | |
| 5,510,036 A | 4/1996 | Woyciesjes et al. | |
| 5,686,276 A | 11/1997 | Laffend et al. | |
| 6,136,576 A | 10/2000 | Diaz-Torres et al. | |
| 6,232,512 B1 | 5/2001 | Haas et al. | |
| 6,245,879 B1 | 6/2001 | Kelsey et al. | |
| 6,358,716 B1 | 3/2002 | Bulthuis et al. | |
| 6,361,983 B1 | 3/2002 | Ames | |
| 7,919,658 B2 * | 4/2011 | Adkesson et al. | 568/868 |
| 2004/0198965 A1 | 10/2004 | Mollee et al. | |
| 2004/0260125 A1 | 12/2004 | Seapan et al. | |

FOREIGN PATENT DOCUMENTS

| | | |
|---|---|---|
| WO | WO 00/24918 | 5/2000 |
| WO | WO 01/25467 A1 | 4/2001 |
| WO | WO 01/73097 A2 | 10/2001 |

OTHER PUBLICATIONS

Ghoreishi, S. M., et al., "Characterization and Reduction of Chromophores in Pulp Mill Effluents", Sci. Iran., vol. 4(3):131-138 Oct. 1997.
House, H. O., "Catalytic Hydrogenation and Dehydrogenation, Modern Synthetic Reactions", Second Ed., W. A. Benjamin: Menlo Park, CA, pp. 1-15 (1972).
Abstract of JP 06165924, published Jun. 14, 1994.
Non-final Office Action mailed Sep. 19, 2006, in U.S. Appl. No. 10/839,188, filed May 5, 2004.
Final Office Action mailed Apr. 20, 2007, in U.S. Appl. No. 10/839,188, filed May 5, 2004.
Non-final Office Action mailed Aug. 31, 2007, in U.S. Appl. No. 10/839,188, filed May 5, 2004.
Final Office Action mailed Apr. 14, 2008, in U.S. Appl. No. 10/839,188, filed May 5, 2004.
Final Office Action mailed Aug. 10, 2009, in U.S. Appl. No. 10/839,188, filed May 5, 2004.
Examiner's Answer mailed Mar. 25, 2010, in U.S. Appl. No. 10/839,188, filed May 5, 2004.
Decision on Appeal mailed Dec. 2, 2010, in U.S. Appl. No. 10/839,188, filed May 5, 2004.
Notice of Allowance mailed Dec. 6, 2010, in U.S. Appl. No. 10/839,188, filed May 5, 2004.

* cited by examiner

*Primary Examiner* — Rosalynd Keys

(57) ABSTRACT

A process for purifying 1,3-propanediol from the fermentation broth of a cultured *E. coli* that has been bioengineered to synthesize 1,3-propanediol from sugar is provided. The basic process entails filtration, ion exchange and distillation of the fermentation broth product stream, preferably including chemical reduction of the product during the distillation procedure. Also provided are highly purified compositions of 1,3-propanediol.

13 Claims, No Drawings ly-produced 1,3-PROPANEDIOL

PURIFICATION OF BIOLOGICALLY-PRODUCED 1,3-PROPANEDIOL

This application claims the benefit of U.S. Provisional Application No. 60/468,231, filed May 6, 2003.

FIELD OF THE INVENTION

This invention relates to a process for the purification of biologically-produced 1,3-propanediol from the fermentation broth of an organism which is able to synthesize 1,3-propanediol. Further, this invention relates to a composition comprising substantially purified 1,3-propanediol.

BACKGROUND OF THE INVENTION

The polyol 1,3-propanediol (PDO) is a monomer useful in the production of a variety of polymers including polyesters, polyurethanes, polyethers and cyclic compounds. The polymers are ultimately used in fibers, films, coatings, composite materials, solvents, anti-freeze, copolyesters and other value-added applications.

1,3-propanediol may be produced synthetically or by fermentation. A variety of chemical routes to generate 1,3-propanediol are known. For example, 1,3-propanediol may be generated from 1) ethylene oxide over a catalyst in the presence of phosphine, water, carbon monoxide, hydrogen, and an acid; 2) by the catalytic solution phase hydration of acrolein followed by reduction; or 3) from hydrocarbons (such as glycerol) reacted in the presence of carbon monoxide and hydrogen over catalysts having atoms from Group VIII of the Periodic Table.

1,3-propanediol produced biologically via fermentation is known, including in U.S. Pat. No. 5,686,276, U.S. Pat. No. 6,358,716, and U.S. Pat. No. 6,136,576, which disclose a process using a recombinantly-engineered bacteria that is able to synthesize 1,3-propanediol during fermentation using inexpensive carbon sources such as glucose or other sugars.

Both the synthetic and fermentative routes to producing 1,3-propanediol generate residual materials that can compromise the quality of the polymers produced from this monomer. Particularly, 1,3-propanediol produced via fermentation contains residual organic impurities that contribute to color and odor aspects in the polyol, and ultimately in the polymers made therefrom.

Fisher et al. disclose in WO 00/24918 a method for purifying a polyol product from a culture generated by a polyol-producing microorganism. The method employs a pretreatment operation that includes microbial cell separation without killing or disrupting the microbes, in combination with removal or deactivation of proteinaceous material. Subsequent purification steps include further removal or deactivation of proteinaceous materials using methods such as froth flotation or flocculation, followed by absorption/adsorption, with further treatments including ion exchange chromatography, activated carbon treatment, evaporative concentration, precipitation and crystallization. The primary goal of the Fisher methodology is to remove proteinaceous contaminants to below a negligible level so that the purified polyol will be suitable for use in food grade products.

George et al. disclose in U.S. Pat. No. 5,034,134 a method for separating impurities from ethylene glycol product streams, particularly aliphatic organic acids, by contacting the ethylene glycol product stream with suitable semi-permeable membranes. A primary goal of the method is to remove UV absorbing molecules and UV absorbing precursors so as to make the purified ethyl glycol monomers suitable for the manufacture of polyesters.

A process for reclaiming lower glycols such as monoethylene glycol, 1,2-propylene glycol and 1,3-propanediol from operative fluids such as antifreeze solutions, heat transfer fluids, deicers, lubricants, hydraulic fluids, quenchants, solvents and absorbents, by contacting the fluid with semi-permeable membranes under reverse osmosis is disclosed in George et al, U.S. Pat. No. 5,194,159.

Haas et al., U.S. Pat. No. 5,334,778, disclose a process for the production for 1,3-propanediol produced from 3-hydroxypropionaldehyde in the presence of a fixed bed or suspension hydrogenation catalyst, wherein the residual carbonyl content of the purified 1,3-propanediol is disclosed to be below 500 ppm.

A process for the treatment of aqueous solutions of polyhydric alcohols to remove heavy metal components, oils and organic contaminants is disclosed in U.S. Pat. No. 5,510,036, Woyciesjes et al., wherein the process comprises a series of pH adjustments of the aqueous solution and additions of various precipitating, flocculating or coagulating agents. Precipitated contaminants are removed from the aqueous solution using filtration means, optionally followed by an ion exchange step.

Haas et al., U.S. Pat. No. 6,232,512 B1, is directed to a method for reducing the content of acetals or ketals in alcohol-containing reaction mixtures. The method comprises hydrogenation of the reaction mixture containing cyclic acetal or ketal with a 1,3-dioxo structure using a Pd and/or Ru activated carbon catalyst, on a trickle-bed reactor at a pH of about 6.5 to 7.0.

A process for preparing 1,3-propanediol-based polyester is disclosed in Kelsey et al., U.S. Pat. No. 6,245,879 B1. The process entails first polymerizing terephthalic acid and a molar excess of 1,3-propanediol to produce polytrimethylene terephthalate, wherein the excess 1,3-propanediol is recovered from the distillate of the reaction by pH adjustment and further distillation. The recovered 1,3-propanediol is then recycled to the original polymerization reaction stream for further reaction with terephthalic acid. Optionally, the reaction stream can be further treated with a borohydride.

Anderson et al., WO 01125467A1 disclose a fermentation medium containing an energy source, a source of inorganic nitrogen, phosphate and biotin, and at least one metal selected from an alkali metal, an alkaline earth metal and transition metals. The disclosed medium is stated to be conducive to supporting the synthesis of polycarboxylic acids, polyols and polyhydroxy acids via fermentation methods.

U.S. Pat. No. 4,380,678, to Sirkar, A. K., discloses a multi-staged process for conversion of aldoses polyols. The process first catalytically hydrogenates the aldose in a fixed bed reaction using high activity nickel catalysts, while adjusting the pH to alkaline conditions. The resulting alditols are then catalytically hydrocracked in a second stage fixed bed reaction. Reaction products are recovered in a separation step, and unconverted heavy alditol can be recycled to the second stage fixed bed zone for further hydrogenolysis.

A need exists in the art for a means to efficiently and economically obtain highly purified biologically-produced 1,3-propanediol from fermentation broth, in order that monomers of sufficient purity may produce useful, high-quality polymers that can be obtained by such biological methods. A further need exists in the art to obtain highly purified compositions of 1,3-propanediol derived from any source, including biological or chemical sources, for certain end uses of the diol including polymerization into polymers used for fabrics, and other applications.

SUMMARY OF THE INVENTION

The invention is directed to a process of purifying biologically-produced 1,3-propanediol from the fermentation broth of an organism able to produce 1,3-propanediol, comprising the steps of: a) subjecting the fermentation broth to filtration; b) subjecting the product of step a to ion exchange purification wherein anionic and cationic molecules are removed; and c) subjecting the product of step b to a distillation procedure comprising at least two distillation columns wherein one of said distillation columns removes molecules having a boiling point exceeding the boiling point of 1,3-propanediol and the other of said distillation columns removes molecules having a boiling point below the boiling point of 1,3-propanediol.

In a preferred mode, the invention is further directed to a process of purifying biologically-produced 1,3-propanediol from the fermentation broth of an organism able to produce 1,3-propanediol, comprising the steps of: a) subjecting the fermentation broth to ceramic crossflow microfiltration wherein cellular biomass of the organism is removed from the fermentation broth; b) subjecting the product of step a to ultrafiltration wherein molecules having a molecular weight greater than about 5000 Daltons are removed; c) subjecting the product of step b to nanofiltration using spiral wound polymeric membranes wherein molecules having a molecular weight greater than about 200 Daltons are removed; d) subjecting the product of step c to two series of ion exchange procedures, wherein each series comprises exposing the product of step c to a strong acid cation exchange followed by a weak base anion exchange resin; e) reducing the amount of water in the product of step d by evaporation; f) subjecting the product of step e to a mixed ion exchange procedure by exposing the product to a resin composition comprising a strong cation exchange resin mixed with a strong base anion exchange resin; g) subjecting the product of step f to a series of two distillations wherein compounds having a boiling point exceeding that of 1,3-propanediol are removed in one distillation column and compounds having a boiling point below the boiling point of 1,3-propanediol are removed in the other distillation column; h) subjecting the product of step g to a hydrogenation reaction; i) and subjecting the product of step h to a series of two distillations wherein in one distillation compounds having a boiling point exceeding that of 1,3-propanediol are removed and in the other distillation compounds having a boiling point below that of 1,3-propanediol are removed.

A further aspect of the invention relates to a composition comprising biologically-produced 1,3-propanediol having a concentration of total organic impurities in said composition of less than about 400 ppm; preferably less than about 300 ppm; and most preferably less than about 150 ppm.

A further aspect of the invention relates to a composition comprising 1,3-propanediol having at least one of the following characteristics: 1) an ultraviolet absorption at 220 nm of less than about 0.200 and at 250 nm of less than about 0.075 and at 275 nm of less than about 0.075; or 2) a composition having L*a*b* "b*" color value of less than about 0.15 and an absorbance at 275 nm of less than about 0.075; or 3) a peroxide composition of less than about 10 ppm; or 4) a concentration of total organic impurities of less than about 400 ppm.

A further aspect of the invention relates to a composition comprising 1,3-propanediol having a concentration of total organic impurities in said composition of less than about 400 ppm; preferably less than 300 ppm; and most preferably less than about 150 ppm.

DETAILED DESCRIPTION OF THE INVENTION

All references cited within this disclosure are incorporated herein by reference in their entirety.

An aspect of the present invention provides a process to obtain purified biologically-produced 1,3-propanediol from the fermentation broth of an organism that is able to synthesize 1,3-propanediol. The process comprises many steps, some of which must be carried out sequentially, and some of which may be carried out in varying order. The terms used in this application shall be accorded the following definitions:

The terms 1,3-propanediol, 1,3-propane diol, 3 G, propanediol, polyol, and PDO are all used interchangeably within this disclosure.

"Substantially purified," as used by applicants to describe the biologically-produced 1,3-propanediol produced by the process of the invention, denotes a composition comprising 1,3-propanediol having at least one of the following characteristics: 1) an ultraviolet absorption at 220 nm of less than about 0.200 and at 250 nm of less than about 0.075 and at 275 nm of less than about 0.075; or 2) a composition having L*a*b* "b*" color value of less than about 0.15 and an absorbance at 270 nm of less than about 0.075; or 3) a peroxide composition of less than about 10 ppm; or 4) a concentration of total organic impurities of less than about 400 ppm.

"Biologically-produced" means that the 1,3-propanediol is synthesized by one or more species or strains of living organisms, including particularly strains of bacteria, yeast, fungus and other microbes. The present method of purification has been demonstrated based upon use of the fermentation broth generated by a genetically-engineered *Escherichia coli* (*E. coli*) previously disclosed by applicants, as disclosed in, for example, U.S. Pat. No. 5,686,276. It is contemplated, however, that other single organisms, or combinations of organisms, could be developed to biologically produce 1,3-propanediol, and that the process disclosed herein would effectively substantially purify the 1,3-propanediol produced into the fermentation broth of such organisms.

It is further contemplated that the purification process disclosed herein by applicants is capable of effectively purifying glycols other than 1,3-propanediol; particularly including ethylene glycol, diethylene glycol, triethylene glycol, 1,2-propylene glycol, dipropylene glycol, tripropylene glycol, neopentyl glycol and bisphenol A.

"Fermentation" refers to a system that catalyzes a reaction between substrate(s) and other nutrients to product(s) through use of a biocatalyst. The biocatalysts can be a whole organism, an isolated enzyme, or any combination or component thereof that is enzymatically active. The "biocatalyst" initiates or modifies the rate of a chemical reaction between substrate(s) and other nutrients to product(s).

A "b*" value is the spectrophotometrically determined "Yellow Blue measurement as defined by the CIE L*a*b* measurement ASTM D6290.

Unless otherwise stated, all percentages, parts, ratios, etc., are by weight. Trademarks are shown in upper case. Further, when an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed.

General Description of the Purification Process

The general inventive process relates to the purification of 1,3-propanediol from the fermentation broth of an organism that is able to synthesize this compound at a commercially viable level. For purposes of disclosing the invention, applicants will describe the fermentation of glucose to propanediol using a genetically engineered *Eschericia coli* developed and previously disclosed by applicant.

The general fermentation process can utilize any number of commercially available carbohydrate substrates, such as partially hydrolyzed cornstarch available, for example, from commercial corn mills. A genetically-engineered *Eschericia coli* is able to metabolize this substrate for growth, metabolic energy and the production of 1,3-propanediol. Fermentation methodology is well-known in the art, and can be carried out in a batch-wise, continuous or semi-continuous manner. The end-cycle fermentation contents is optionally heated in an external heat exchanger to kill the microorganisms prior to removal of the microbial biomass and further purification of the diol product.

A preferred version of applicants' general process is described below:

1. Filtration

Filtration is the initial step employed in applicants' process, to remove cellular biomass, particulates and high molecular weight contaminants from the fermentation media. Many methods of filtration can be utilized by the user. A preferred method adopted by applicants utilizes a three step filtration procedure, as follows:

The material can first be microfiltered using, for example, ceramic elements to remove biomass.

The microfiltered broth can then be subjected to an ultrafiltration step which removes compounds having a molecular weight exceeding about 5000 Daltons.

The ultrafiltered broth can then be further subjected to a nanofiltration system which utilizes membrane element to remove compounds exceeding about 200 to 400 Daltons, for example, high molecular weight sugars and salts.

The washed retentate from the above filtrations can be dried and landfilled.

2. Ion Exchange

The filtered broth containing the propanediol and other fermentation by-products is then subjected to an ion exchange purification, preferably, utilizing a series of separate ion exchange purification steps. First, for example, the broth can be exposed to a strong acid cation exchange resin, followed by exposure to a weak base anion exchange resin. This series is preferably repeated one time.

In a preferred embodiment, the broth is then optionally subjected to an evaporation step, for the purpose of reducing the amount of water in the both to less than about 25%.

The broth then can be exposed to a mixed ion exchange procedure using a mixed resin composition comprising a strong acid cation exchange resin and a strong base anion exchange resin.

3. Distillation

Next, a refining process is conducted in order to remove contaminates having boiling points greater than and less than that of 1,3-propanediol. For example, a preferred distillation process employing 4 columns can be used. First, a distillation column removes additional water, the overhead water stream is disposed of, and the bottoms of the column can be fed to a second distillation column where the heavy impurities, primarily glycerol and residual sugars, are removed.

In one particularly preferred embodiment of the invention, the overheads from this second column then can be optionally subjected to chemical reduction, for example via a hydrogenation reactor, which converts near-boiling impurities into compounds that can be separated in subsequent distillation columns. Additionally, organic impurities with characteristics that are problematic to the final application of the dial are reduced to less problematic species.

A third distillation column is then able to remove light impurities overhead, from which the bottoms are sent to a final, forth column where the purified product is taken overhead to storage. The bottoms from this fourth column can be optionally recycled to the second column in the refining train.

All four distillation columns can be operated under vacuum to reduce operating temperatures to minimize unwanted reactions and product degradation.

The product of the final distillation column will comprise purified 1,3-propanediol.

Each of these steps now will be described more specifically below.

Microfiltration

In the separation of 1,3-propanediol from fermentation broth, it is first desirable to remove the biomass from the fermentation material. Several well-known methods are known in the art to remove particulate materials such as cell biomass and particulate material from liquid media; for example, centrifugation or variations of filtration procedures. A preferred first step is microfiltration, for example, cross-flow microfiltration using ceramic elements. Ceramic element microfiltration is a well established technology with numerous commercial scale applications, including biomass separation from fermentation broth. Ceramic element cross-flow microfiltration offers a number of inherent advantages in a commercial setting.

A preferred microfiltration system consists of ceramic elements that are housed in preferably stainless steel housings. The elements consist of a ceramic support with coarse porosity that is coated with several membrane layers. The preferred final membrane layer that accomplishes the actual filtration is a thin ceramic layer (about 0.5 to 2.0 microns thick) that is applied to the surface of the channels in the ceramic element. These membranes are commercially available, for example, from Membraflow Corporation, a firm headquartered in Aalen, Germany. The membrane support is composed of alpha alumina with a macroporous structure that is highly permeable, and very strong. The support has parallel channels through which the liquid to be filtered flows at high velocity. The filtrate, or permeate, flows through the membrane, which is the surface layer of those channels. The permeate then flows through the support into the housing which holds the elements in place. It is collected from the housing into a header system and flows into a collection tank. Optionally, the stream containing the solids that are filtered out (the retentate) passes out of the channel into a header where it can be mixed with feed and recycled.

The effect of temperature on microfiltration flux has been found to be significant. Differences as small as 10° F. have had an impact on the system flux rates with higher temperatures increasing the flux. Temperature should be maintained at or above 165° F. The upper maximum is dependent on the limits of the equipment and the contribution of color to the broth.

It will be necessary to clean the microfiltration filters as recommended by the manufacturer, and according to the user's individual process parameters.

Ultrafiltration

An intermediate filtration step, subsequent to removal of the biomass and cell debri, and prior to nanofiltration of the filtrate, may be desirable. The goal of this step is to remove contaminants of fairly high molecular weight, so that the nanofiltration step will be efficient and effective. Although many intermediate filtration methods are available, a preferred system of ultrafiltration selected by applicants includes membrane filtration with a molecular weight cut off of approximately 5000 Daltons, under a pressure of approximately 60 psi.

In a preferred embodiment, microfiltration comprises removing molecules having a size greater than 0.2 microns.

Nanofiltration

When the microfiltration and ultrafiltration of the fermentation broth is complete, the broth is essentially free of insoluble material. It is the intent of the nanofiltration process to remove as much impurity as is practical prior to further purification and distillation. The major impurities at this point are residual saccharides, proteins, media salts, and components produced by the fermentation including ammonia salts of organic acids, glycerol, 1-2-4 butanetriol, and UV absorbers. Applicants' preferred method to remove the bulk of these impurities is nanofiltration using spiral wound membranes. Applicants' preferred nanofiltration uses size selective polymeric membranes that also reject strongly charged molecules as its methods for separating the components. Based on applicants' data with the current organism, nearly 100% of the residual saccharides and proteins can be removed from the nanofiltration permeate, UV absorbers at 460 nm (visible range) are 93% rejected by the membranes, and ionic components can be 40-60% rejected in total with divalent cations being 90% rejected and weak organic acids approximately 33% rejected. The smaller molecular weight components with little or no net charge (such as propanediol and glycerol) pass through the membranes completely. To accomplish these separations, the pressure difference across the membrane must be greater than the osmotic pressure exerted by the difference in salt concentrations. Applicants have found that this pressure difference can range from 200 psi to 600 psi with higher pressures giving higher flux rates, but usually resulting in faster fouling.

The polymeric membranes preferred by applicants have both positives and negatives in operating performance. On the positive side the membranes can handle large swings in pH's without damage. However, it should be noted that the molecular weight cutoff (the average size that molecules equal to or above are rejected) will change with pH. The more acidic the product stream, the smaller the cutoff. Another positive aspect is that the membranes are relatively inexpensive compared to ceramic. This is somewhat offset by their shorter lifespan (6 months versus 5-10 years). The upper temperature limit for polymeric membranes is significantly below that of ceramic elements with a typical upper limit of 150° F. This limit is dependent on the manufacturer and can be lower. Polymeric membranes cannot be exposed to chlorides such as bleach or other oxidizers. In addition, the membrane is subject to irreversible fouling from dissolved metals such as iron. The fouling is far more prevalent when iron is present in the cleaning water rather than the process stream.

The elements are available commercially, for example, from Osmotics Desal. Preferably, the elements used in this step have a molecular weight cutoff of approximately 200 to 400 Daltons.

Ion Exchange

Following the filtration step(s), the major remaining non-propanediol components in the broth are glycerol, 1-2-4 butanetriol, weak ions, and UV absorbers. Ion exchange is the next step used in applicants' invention to remove further of these contaminants. Several general ion exchange methodologies are well-known in the art of purification. A preferred technology employed by applicants to remove the ions and UV absorbers is ion exchange using Styrene-Divinylbenzene based resin. Applicants believe that removal of salts enhances the color stability of products when subjected to heat stress.

It is the intent of the ion exchange process to remove as much impurity as is practical from the nanofiltered broth prior to distillation. The major targeted impurities are weak ions not removed by nanofiltration and as much of the remaining UV absorbers as possible. To accomplish this, ion exchange resins are used that exchange hydrogen ions attached to the surface of the bead for the cations in the broth and hydroxide ions for the anions in the broth. This occurs because the hydrogen and hydroxide ions are very weakly held by the resin which prefers the stronger charge of the ions in the broth. In addition to the ion exchange capacity of the resin, the pores of the resin allow molecules of a certain size range to be absorbed and retained. Most of the UV absorbers present in the broth after nanofiltration fall in this range.

As is well-known in this art, once all the available sites on the resin have exchanged ions, the resin is exhausted and must be "regenerated." This is done by pumping acid through the cation beds and caustic through the anion beds. The high concentration of hydrogen ions in the acid overwhelm the attraction for the higher charged ions causing them to be released. These cations are discharged as salts of the acid anion (chlorides in this case). The same is true for the anion resin, replacing the broth anions with hydroxides and discharging them as sodium salts. In addition to reactivating the exchange sites, the molecules absorbed by the resin are displaced by the regenerants and discharged with the salt wastes. Periodically, the resins are expanded by cross-regeneration to help purge the absorbed components. Cross-regeneration is done by reversing the chemicals (caustic for the cation and acid for the anion) prior to normal regeneration.

The resin can be constantly cycled until enough of the sites become irreversibly fouled reducing capacity below acceptable limits. The spent resin is replaced with fresh resin and the cycles begin again. Resin life is often described in terms of the number of cycles, which varies according to individual application. User specifications will accompany the resins, which are readily available commercially.

The most effective and cost sensitive method found to accomplish the propanediol purification involves a series of ion exchange columns configured in the following sequence; Strong Acid Cation (SAC), Weak Base Anion (WBA), Strong Acid Cation (SAC), Weak Base Anion (WBA), and a "Mixed Bed" composed of a mixture of Strong Acid Cation and Strong Base Anion (SBA) (described below). This is called a CACA configuration with a Mixed Bed Polish. An evaporation step (described below) optionally occurs prior to adding the broth to the Mixed Bed.

Preferably, a first "pair" of strong Cation/weak Anion columns will most efficiently affect the bulk of the impurity removal. Because hydrogen ions are released by the cation resin, the broth becomes very acidic as it passes through the cation column. When the ionic load of the feed is high like our fermentation broth, the broth becomes acidic enough to mimic regeneration conditions and limits how pure the product can get out of one cation pass. As the broth passes through the first anion column, the hydroxides released neutralize the hydrogen ions from the cation column producing water. This allows the first anion column to do more salt splitting since it does not mimic the regeneration conditions so quickly. The discharge from the first anion should be strongly basic. Because of the self-limiting nature of the first pair, a second pair is preferred to get a highly pure product. In addition, by having two pairs in series, it allows the first pair to use its full capacity before regeneration. When the first pair is exhausted, the feed is switched to the second pair and the regenerated pair is valved in as the next in the series.

Evaporation

In a preferred embodiment relating to the purification of 1,3-propanediol from fermentation, the product stream is concentrated from about 90% moisture to about 20% moisture prior to distillation. For cost reasons, it is particularly preferred to conduct this concentration step prior to the final ion exchange mixed bed step. The water to be removed comes from fermentation, microfiltration diafiltration, nanofiltration diafiltration, ion exchange sweeten off, and any water incorporated from cleaning the upstream systems. Many means of reducing water content in liquids is known. One preferred technology is a mechanical recompression (MR) evaporator.

Applicants have learned that one of the best feeds to distillation is produced by low temperature evaporation as measured by UV absorbance and visible color profile. Earlier in the purification process, there will be visible brown color in the evaporation product with a relatively high level of UV absorbance. Improvements in the evaporation vacuum system can lower absorbance at 460 nm to zero by means of lowering the temperatures in the evaporator with higher vacuum and reduced evaporation time.

One key to the design of a commercially effective evaporation system is the maximum temperature allowed for the product to achieve. Applicants' data indicates that a maximum temperature of 155° F. is safe and will not significantly increase the UV absorbance at 260 nm even if maintained for long periods of time (up to 24 hours). However, Applicants' data also indicates that significant UV absorbance is created at a temperature of 190° F. over long periods of time.

To further complicate the time-temperature issue, the distillation process following evaporation operates at even higher temperatures (230-300° F.) for significant lengths of time. Any improvement in distillation feed quality could be insignificant to final product quality. Thus, design of evaporation equipment must be based on net impact to final product quality. A higher temperature limit of approximately 190° F. is preferred, however, this value can be varied by the user to achieve varying final product quality specifications.

The principle of a mechanical recompression evaporator is to use a large blower or fan to recompress the vapors exiting a flash separator (either under vacuum or slight pressure). By recompressing the vapors the temperature of the vapor is elevated. This hotter vapor is then used in place of steam as the driving force for further evaporation. The system is very energy efficient, often achieving energy usage as low as 75 BTUs per pound of water evaporated (horsepower and preheat steam combined).

In a preferred case, a vacuum system will be selected and a two-stage condenser off the last stage will be used. The first condenser will be designed to recover and recycle any PDO boiled off. The second condenses the remaining vapors. The heat from the condensate off the evaporator will be recovered with heat reclaim heat exchangers or used where hot water is required.

Polish with Mixed Ion Exchange

After subjection of the fermentation broth to ion exchange, for example as described above to four ion exchange columns of the CACA system, and optionally to evaporation, subjection additionally to a strong base anion is preferred for maximum purification. Thus, by adding the strong base mixed bed polish column, applicants gain the best possible quality while maintaining a low operating cost process. The mixed bed column is as its name implies. The cation and anion resins are mixed together in proportions to match their individual exchange capacities. By mixing the resins, the pH of the product flowing through the bed remains neutral throughout the length of the column. Not only does this allow for maximum exchange, it also reduces the potential for chemical reactions caused by extremes in pH. These reactions usually result in UV absorbers and the mixed bed column acts as a final polisher prior to evaporation and distillation. Regeneration of the mixed bed is unique in that the resins must first be separated before introducing the chemicals following sweetening off with water. Regeneration preferably can be done by upflowing the resin bed with water to drive the lighter anion resin to the top of the column. Once separated, caustic is pumped into the top of the column and acid into the bottom. The waste salt streams combine in the middle of the column and are extracted through a center header. The resins are rinsed in the same directions as the chemicals and then re-mixed by bubbling air from the bottom of the column. The column is then ready for product again. The mixed bed polish can preferably be located after the evaporation step to concentrate the impurities to increase the potential for removal. In addition, UV absorbers created by evaporation can be partially removed by the resin prior to distillation.

Sizing of an Ion Exchange system is usually based on two things, pressure drop and desired cycle time. The feed flow rate and viscosity will dictate the cross-sectional area and allowable bed depth required for the columns to keep the feed pressure below the target limit (approximately 50 psig). The cycle time of the resin must allow sufficient time for proper sweetening off, regeneration, and rinsing. Depending on the product, it takes some time for the water, product, and chemicals to migrate into and out of the resin beads during the respective steps in the cycle. These time limits are defined by the resin manufacturer. Ion exchange resins with varying specifications are commercially available from many sources.

Distillation

Distillation is the final step in applicants' process. Many variations and methodologies of distillation technology are well-known in the art. Applicants' preferred system comprises a distillation train consisting of four columns to refine the partially purified product from fermentation and middle separation steps of the biologically-produced PDO process. Distillation is a well-characterized and readily available technology used to purify products by removing impurities due to their boiling point differences. There will be many impurities in the PDO product feed prior to the distillation train, including water, glycerol, dextrose, and other light boilers and heavy boilers. Some of these impurities decompose or react at high temperatures and can cause color problems in a polymerized final product. Distillation allows the separation of these impurities from a product at lower temperatures and minimizes the undesirable reactions occurring in the columns. Also, in a preferred embodiment, in order to produce 1,3-propanediol of the highest purity, a chemical reduction such as hydrogenation step (see below) is optionally inserted prior to the final distillation column(s). Applicants' most preferred scheme includes four distillation columns, with chemical reduction, preferably hydrogenation occurring between column 2 and column 3. For example, in this scheme, column 2 overheads can be sent to a hydrogenation reactor system where the color impurities react with hydrogen over an NI/Silica-Alumina catalyst and are converted to light impurities, such as alcohols. These impurities are then removed from the refining train as column 3 overheads. With hydrogenation, the user can operate column 2 at a higher bottom temperature and at a lower purge because one can rely on the hydrogenation reactor instead of column 2 purge to remove the impurities. The preferred chemical reduction or hydrogenation step is the subject of a separate application, co-owned and concurrently filed by applicants, U.S. 60/468,212, entitled "Hydrogenation of Fermentatively-Produced 1,3-propanediol," which is hereby incorporated by reference in its entirety.

In general, applicants' preferred distillation train consists of 4 vacuum distillation columns and a hydrogenation reactor system between columns 2 and 3. The objective of the distillation train is to distill in-spec PDO off the crude product from the previous ion exchange step. The crude product, which contains about 20% water if an evaporation step is used, is stored in a feed tank from where it is pumped to column 1. The water in the crude product is removed as overheads in column 1. In column 2, glycerol, sugars and other high boilers are separated from PDO and purged out of the system as column 2 bottoms. The distillate from column 2 is processed through a chemical reduction step, e.g., a hydrogenation reactor system, where color-forming impurities can be converted to more easily separated low boilers. Column 3 then removes low boilers and residual water that come from column 1 and from side reactions in the columns. The bottom product from column 3 is fed to column 4 where the final rectification takes place to reduce the UV values of the distillate to meet the individual users' product specifications.

Column 1 (Water Column)

Column 1 is a packed distillation column and its objective is to remove the water from the feed as overheads and to reduce the water in the bottoms to less than 1000 ppm. The column is preferably operated under vacuum and the pressure at the top is maintained at about 55 mm Hg A so overhead water can be condensed with cooling tower water. The overhead vapor is condensed on the tube side of column 1 condenser while cooling water is circulated through the shell side. The condensate, mainly water, can be sent to a reflux drum by gravity. It is preferred to have low pressure drop across the column to keep the temperature at the bottom as low as possible. A falling film reboiler can be used to minimize the hold-up time in the reboiler and therefore the undesirable reactions in the bottom of the column. Steam (200 psig) can be fed to the reboiler to provide the necessary boilup and to control the temperature at the bottom of the column at about 145° C. The bottoms of the column is pumped to column 2.

Column 2 (Heavies Column)

Column 2 is also a packed column and its objective is to remove the heavy impurities, mainly glycerol, sugars and other impurities coming from fermentation or generated by the undesirable reactions in the columns. As in column 1, it is important to keep the temperature and liquid hold-up in the bottom as low as possible to reduce degradation and side reactions. A falling film reboiler can be also used here. The temperature at the bottom is controlled at about 165° C. The column bottoms consisting of glycerol, PDO and heavy boilers is purged to a storage tank. The overhead vapor, which contains >99% PDO, is condensed and collected in a reflux drum. The overheads which are not refluxed to the column can be sent to a hydrogenation reactor system. The column is operated at 20 mm Hg A and at about 120° C. at the top. This column can also remove about 85% of the sulfur coming in with the crude feed.

Chemical Reduction

Chemical reduction of contaminants remaining in the PDO stream is useful, particularly if it occurs prior to the last stages of distillation, to remove final impurities. Chemical reduction methods include any method capable of removing double bonds left in the PDO molecules in the product stream. Hydrogenation and sodium borohydride (hydroboration) methods, for example, are particularly well-known in the art.

Catalytic hydrogenation, applicants' preferred method, is the reaction of a compound with hydrogen in the presence of a catalyst. This reaction reduces residual organic compounds and offers the advantages of widespread applicability and experimental simplicity and thus is used for many chemical processes. For instance, hydrogenation has been used to remove color-causing compounds in the production of certain products from wastewater streams of the kraft pulp mill process (Ghoreishi et al., Characterization and Reduction of Chromophores in Pulp Mill Effluents. *Sci. Iran.* 4(3):131-138 (1997)). A variety of substances are poisons for hydrogenation catalysts; the most commonly encountered being mercury, divalent sulfur compounds, and, to a lesser degree, amines (H. O House, *Modern Synthetic Reactions*, Second ed., W. A. Benjamin: Menlo Park, Calif., pp 1-15 (1972)).

The process entails contacting the PDO-containing mixture with hydrogen gas in the presence of a catalyst, which will improve color of the polyol, raise the pH of the mixture, and reduce sulfur. These changes lead to improved performance of the PDO in a wide variety of applications.

An advantage of introducing a hydrogenation step after fermentatively producing 1,3-propanediol is obtaining better control over the intrinsic viscosity (IV) and the "color" index of the ultimate polymer by removing color-forming bodies. Not only does the treated 1,3-propanediol and its oligomers show "colorless" attributes, but also, the polymeric materials made from such entities having at least one repeat unit of the monomer show a reduced 'yellowness index' or a reduced color. In the most preferred mode, for the bio-based PDO and/or oligomers the hydrogenation step is coupled with a final distillation step.

By the terms "color" and "color bodies" is meant the existence of visible color that can be quantified using a spectrocolorimeter in the range of visible fight, using wavelengths of approximately 400-800 nm, and by comparison with pure water. Color precursors in PDO are not visible in this range, but contribute color after polymerization in the PDO. Polymerization conditions can have an important effect on the nature of color production. Examples of relevant conditions include the temperatures used, the catalyst and amount of catalyst. While not wishing to be bound by theory, we believe color precursors include trace amounts of impurities comprising olefinic bonds, acetals and other carbonyl compounds, peroxides, etc. At least some of these impurities may be detected by such methods as UV spectroscopy, or peroxide titration.

"Color index" refers to an analytic measure of the electromagnetic radiation-absorbing properties of a substance or compound.

"Hydrogenation reactor" refers to any of the known chemical reactors known in the literature, including but not limited to shaker-tubes, batch autoclaves, slurry reactors, up-flow packed bed, and trickle flow packed bed reactors.

Hydrogenation can be achieved by contacting the PDO with hydrogen in the presence of a catalyst at elevated temperatures and pressures. The catalyst can be comprised of elements of Group VIII of the periodic table. More specifically, any of the following metals Ni, Co, Ru, Rh, Pd, Ir and Pt with or without various promoters are also effective catalysts for this purpose. Various mixed oxides such as copper chromate are an effective catalyst for color removal. Hydrogenation catalysts are known in the art and are extensively covered in "*Handbook of Heterogeneous Catalytic Hydrogenation for Organic Synthesis*" by S. Nishimuru, John Wiley (2001).

The catalyst may be a porous metal structure or supported on a substrate. The catalyst support could be from any support material known in the art, such as carbon, alumina, silica, titania, silica-alumina, silica-titania, titania-alumina, clays, aluminosilicates, water insoluble salts of calcium, barium, barium sulfate, calcium carbonate, strontium carbonate, compounds thereof, and combinations thereof.

The catalyst may have various shapes or sizes, ranging from a fine powder to granules, tablets, pellets, extrudates or other structured supports. The metal catalyst and the support are selected from the group consisting of palladium on carbon, palladium on calcium carbonate, palladium on barium sulfate, palladium on alumina, palladium on titania, platinum on carbon, platinum on alumina, platinum on silica, iridium on silica, iridium on carbon, iridium on alumina, rhodium on carbon, rhodium on silica, rhodium on alumina, nickel on carbon, nickel on alumina, nickel on silica, rhenium on carbon, rhenium on silica, rhenium on alumina, rethenium on carbon, rethenium on alumina and ruthenium on silica. An example of the preferred catalyst is nickel, which may be in the form of a RANEY catalyst (which may be doped with other catalytically active metals) or extrudates supported on silica/alumina.

Hydrogenation may be carried out in various gas-/liquid-/solid-contacting reactors known in the art. These reactors may operate in batch, semi-batch, and flow mode. An industrially advantageous reactor uses a packed bed of catalyst where the liquid and gas flow co-currently or counter-currently, in an up-flow or down-flow (trickle-bed) mode of operations.

In the hydrogenation process, the conversion of the color compounds and their precut cors depends on the duration of contact time with the catalyst. Contact time is represented by the residence time in the batch operations and by the space velocity (LHSV=Liquid Hourly Space Velocity) in the flow reactors.

Temperature also affects the conversion of the color or color-precursor compounds. The conversion increases exponentially with temperature according to the Arrhenius Law. However, since color is a measure of the combined effects of various chromophores, and since the color is measured by the absorption of UV radiation and expressed as a logarithmic function of concentration, the overall dependency of color on temperature deviates from general Arrhenius form and approaches a linear relation. A proper combination of contact time and temperature can achieve a desired color improvement at temperatures as low as 25° C. Temperatures in the range of 25-200° C. can reduce color. However, at higher temperatures, hydrogenolysis of polyols (specifically 1,3-propanediol) starts to generate lighter alcohols (ethanol and propanol) and dioxanes, causing a yield loss of the polyol. At temperatures above 140-150° C., yield loss becomes significant. While effective color reduction can be achieved in the range of 25-200° C., the preferred temperature range is 80-130° C.

Hydrogen consumption is generally very low and depends on the level of impurities present in the crude polyol. Generally hydrogen consumption is within the range of hydrogen solubility in the crude liquid. With the proper selection of temperature and contact time, adequate conversion can be achieved at slightly above atmospheric pressures. Above this level, an additional increase in pressure has minimal effect on the extent of color removal. Color reductions can be achieved at pressures from ambient to 1000 psig, with 200-400 psig being the preferred range of pressure.

The ratio of hydrogen to polyol feed rates does not have a significant effect on the conversion above the stoichiometric required level of hydrogen. Effective color reductions can be achieved at 0.05-100 scc per gram of crude PDO. The preferred range is 0.5-2 scc/g.

The variability of the UV spectra of the crude PDO solution depends on the process that generated the PDO and also on the effectiveness of the purification steps used in post-production and pre-hydrogenation stages. The extent of color reduction depends on the initial color level of the crude PDO solution. For a given color level in the crude PDO solution, the desired color reduction can be achieved by selecting suitable operating conditions for hydrogenation.

Final Distillation

Preferably, following chemical reduction such as hydrogenation, the product stream now can be subjected to final distillation for further removal of additional impurities.

Distillation Column 3 (Intermediates Column)

The objective of column 3 in applicants' most preferred embodiment is to distill off water and further light impurities from the PDO product. The light impurities and water come from column 1 bottoms, from the side reactions in column 2 and from chemical reduction procedure. The light impurities and water along with PDO are purged as column overheads to storage tank for disposal by incineration. The column bottoms is sent to column 4. Column 3 preferably operates at about 35 mm Hg A at the top and at about 145° C. at the bottom. The top temperature of column 3 is preferably about 130° C., depending on the concentration of water and the light impurities.

Distillation Column 4 (Product Column)

The objective of this final column is to provide the final rectification to produce in-spec PDO product. After the light impurities are removed in column 3, the remaining heavy impurities are removed in the bottom section of column 4. The overhead vapor is condensed and collected in a reflux drum. The reflux drum pump pumps some of the condensate back to the column as reflux; the rest is sent as final product through a heat exchanger to heat column 1 feed. The product then can be sent to the product storage tank. The UV absorbance of the distillate can be monitored continuously by an on-line UV analyzer. The bottoms, which contain heavy impurities, can be recycled to the bottom section of column 2. The column preferably operates at about 45 mm Hg A at the top and at about 145° C. at the bottom.

Vacuum System

A common vacuum system can preferably be used for all distillation columns. A two stage system consisting of a steam jet with an after condenser, and the second stage consisting of a liquid ring vacuum pump can be employed. Several options exist for the user relating to the vacuum system selected. Two stages can be used, with the first stage an air eductor or a blower instead of a steam jet, and the second might be a dry screw pump instead of a liquid ring. The non-condensable vapor from the vacuum system can be sent to a vent scrubber before being emitted to the atmosphere in order to meet the air emission requirements. The liquid waste can be collected and disposed of.

Final product quality is affected not only by the separation performance of the distillation columns but also by the numerous chemical reactions occurring within the columns; these reactions are not completely understood, characterized, or quantified. In principle, the three factors controlling these reactions are chemical concentrations, temperatures, and liquid volumes (or residence times). Chemical concentrations are governed by conditions in the columns themselves and by the crude feed quality produced by the separation section (hence the need for specifications on crude feed quality). Temperatures are governed by the concentrations and pressures within the columns, so column pressures have been chosen (15-55 mm Hg) to keep the temperatures as low as possible. Liquid holdups, particularly in column bases where temperatures are highest, are important design variables and should be minimized to the extent possible without sacrificing operability and disturbance rejection (for example, the column reboiler pumps must still function after a sudden loss of column feed, etc). One way to reduce base liquid holdup is to neck down from full column diameter. Regardless of how this is done, it is important that the column base level measurement itself should cover the whole range of base volume, not just some fraction of it.

Purity Characterization of the 1,3-Propanediol

The purified product emerging from applicants' process will be highly purified 1,3-propanediol. The level of purity can be characterized in a number of different ways. For example, measuring the remaining levels of contaminating organic impurities is one useful measure. Applicants' method can achieve purity levels less than about 400 ppm total organic contaminants; preferably less than about 300 ppm; and most preferably less than about 150 ppm. The term ppm total organic purity refers to parts per million levels of carbon-containing compounds (other than 1,3-propanediol) as measured by gas chromatography.

The purified product can also be characterized using a number of other parameters, such as ultraviolet light absorbance at varying wavelengths. The wavelengths 220 nm, 240 nm and 270 nm have been found to be useful in determining purity levels of the composition. Applicants' process can achieve purity levels wherein the UV absorption at 220 nm is less than about 0.200 and at 240 nm is less than about 0.075 and at 270 nm is less than about 0.075.

A b* color value (CIE L*a*b*) of less than about 0.15 in the purified 1,3-propanediol is also accomplished by applicants' process.

And finally, it has been found that the purity of 1,3-propanediol compositions can be assessed in a meaningful way by measuring levels of peroxide. Applicants' process achieves compositions of purified 1,3-propanediol having a concentration of peroxide of less than about 10 ppm.

Applicants believe that the process of the invention, in its preferred mode, will produce highly purified compositions of 1,3-propanediol from any source; including biologically produced and chemically produced compositions.

EXAMPLES

The present invention is further defined in the following Examples. These Examples, while indicating preferred embodiments of the invention, are given by way of illustration only, From the above discussion and these Examples, one skilled in the art can ascertain the essential characteristics of this invention, and without departing from the spirit and scope thereof, can make various changes and modifications of the invention to adapt it to various usages and conditions.

Example #1

Production of 1,3-Propanediol Via an Aerobic Fed-Batch Fermentation

A frozen vial containing a genetically modified *Escherichia coli* production organism (see U.S. Pat. No. 5,686,276) was streaked for isolation onto a nutrient rich agar plate. An isolated small colony was chosen from the streak plate and placed into a 2 L baffled shake flask containing 500 mL of 2YT media. The flask was then incubated at 34° C. and 350 RPM for 10 hours to obtain a biomass concentration of 0.3 gDCW/L (dry cell weight). The seed flask was used to inoculate the seed fermentor.

The seed fermentor is a stainless steel, ASME full vacuum rated, air sparged, pressure vessel with a total volume of 1500 L. The seed fermentor was filled with city water and medium components to an initial volume of 685 L, see Table 1 below for the seed fermentor medium recipe. Once the medium is mixed, the seed fermentor is sterilized in-situ by direct steam injection. The medium is sterilized at 121° C. for 60 minutes. Following sterilization the fermentor is brought to running conditions: 6.8 pH, 33° C., 5 psig back pressure, and an initial dextrose concentration of 25 g/L. Once the fermentor is at running conditions, 50 g of Spectinomycin Dihydrochloride (purchased through Sigma Aldrich) dissolved in 1 L of DI water is filter sterilized into the seed fermentor through a 0.22µ rated sterile membrane filter.

After the Spectinomycin Dihydrochloride was added, the fermentor was inoculated with the shake flask that was referenced earlier in this section. Throughout the seed cycle the pH is maintained at 6.8 with the addition of anhydrous ammonia, the dissolved oxygen (DO) is maintained at 15% relative to saturation, and the temperature is maintained at 33° C. Once the dextrose concentration in the fermentor reaches 10 g/L the carbohydrate feed was started to maintain a dextrose concentration of 5-10 g/L. Once the seed fermentor reaches 6 gDCW/L it is transferred into the production tank.

TABLE 1

Seed and Production Fermentor Medium Recipe

| Media Component | Initial Concentration (g/L) |
|---|---|
| sulfuric acid | 0.55 |
| Phosphoric Acid, 85% | 1.34 |
| KH2PO4*** | 1.4 |
| Citric acid monohydrate | 1.02 |
| MgSO4*7H2O | 0.6 |
| FeSO4*7H2O | 0.400 |
| CaCl2*2H2O | 0.1 |
| Soy Protein 4950 | 0.5 |
| Sigma 204 Antifoam | 0.40 |
| MnSO4 H2O | 0.015 |
| NaCl | 0.005 |
| ZnSO4*7H2O | 0.0005 |
| CuSO4*5H2O | 0.00005 |
| H3BO3 | 0.00005 |
| NaMoO4*2H2O | 0.00005 |

The production fermentor is a stainless steel, ASME full vacuum rated, air sparged, pressure vessel with a total volume of 13,000 L. The production fermentor is filled to an initial volume of 5645 L of city water and the medium recipe is the same as the seed fermentor and is referenced in Table 1 above. The production fermentor medium is sterilized in-situ with direct steam injection, and is held at 121° C. for 60 minutes. Following sterilization the fermentor is brought to running conditions: 6.8 pH, 33° C., 5 psig back pressure, and an initial dextrose concentration of 10 g/L. Once the fermentor is at running conditions, 250 g of Spectinomycin Dihydrochloride (purchased through Sigma Aldrich) dissolved in 2 L of DI water is filter sterilized into the production fermentor through a 0.22µ rated sterile membrane filter.

Following the addition of the antibiotic, the seed is blown into the production fermentor using air pressure. Immediately following inoculation, the carbohydrate feed starts and is controlled to maintain a dextrose concentration in the production fermentor of 5-15 g/L. Throughout the production cycle the pH is maintained at 6.8 using anhydrous ammonia, the DO is controlled at 10% relative to saturation, and the temperature is maintained at 33° C.

One hour after inoculation a 1 g bolus of crystalline vitamin $B_{12}$ (supplied by Roche Vitamins Inc.), dissolved in 10 L of DI water, is filter sterilized into the production fermentor through a 0.22µ rated sterile membrane filter. The $B_{12}$ solution is added to a 20 L stainless steel, pressure rated vessel. The solution is then pushed through the sterile filter by pressurizing the stainless steel vessel with air. A second 11 g bolus of vitamin B12, prepared the same as above, is dosed into the production fermentor once the biomass concentration reaches 4.5 gDCW/L.

The production fermentation cycle is complete within 40-45 hours after inoculation. After the production cycle is complete the biocatalyst optionally can be deactivated by live steam injection into the fermentor. The temperature of the fermentor can be held at 75° C. for 45 minutes to ensure a log-6 reduction in viable organisms. Following the optional deactivation step the broth is sent to filtration to begin the crude PDO refining process.

Throughout the fermentation cycle, a YSI® 2700 Select Biochemistry Analyzer is used to measure the dextrose concentration in grab samples of the fermentation broth. The biomass concentration is measured using the ThermoSpectronic Spectronic 20 D+ Spectrophotometer, throughout the fermentation. The PDO concentration in the broth can be measured using HPLC throughout the fermentation.

Example #2

Microfiltration of Fermentation Broth

The microfiltration set up is a single stage, two modules in series filtration unit that is operated fed-batch. Fermentation broth, for example, from Example #1 is pumped from a microfiltration feed tank to the skid and then recirculated within the membrane loop. Permeate is continuously sent forward to an intermediate storage tank and the retentate recycled back to the microfiltration feed tank. The installed membrane modules are 50 nm pore size, 4 mm lumen Membraflow ceramic elements (Model #22M374R-50, 10.34 m² each). PDO fermentation broth was fed to the skid at 165° F. and maintained at 65 psi system pressure (38-45 psi TMP module #1, 27-37 psi TMP module #2). To minimize the concentration polarization layer, recirculation flow across the ceramic membranes was sustained at 5 m/sec crossflow velocity (~900 gpm). A flow control valve on the retentate return line limits the flow of concentrate back to the microfiltration feed tank to 10 gpm, thereby creating the back pressure for the system. Using the differential between flow totalizers on the inlet feed and outlet permeate lines, the targeted volumetric concentration ratio (VCR) of 12× was monitored and controlled. The microfiltration separates the larger biomass and insoluble materials from the PDO fermentation broth, hence clarifying the product stream of the larger macromolecules suspended in solution. Table 2 depicts the microfiltration operation.

TABLE 2

| Microfiltration operation | | | | |
|---|---|---|---|---|
| | Optical Density | Cell Concentration (gram/L) | Volumetric Concentration Ration | Flux (liters/m²/hr) |
| Feed to Microfiltration | 44.3 | 13.29 | 1 | 194.3 |
| Final Retentate | N/A | 159.48 | 12 | 19.7 |
| Average | | | | 108 |

The current PDO-producing organism has demonstrated an average flux through microfiltration of 108 LMH with a standard deviation of 15-20% (18-20 LMH). There is a rapid drop off in the flux through microfiltration in the early stages of broth concentration, and as the concentration of the initial broth doubles there is 50% decline in flux. This rapid decline in flux tampers off as the targeted 12× VCR is achieved and over the entire concentration an 85-90% loss of flux is consistently observed. The consistency in the VCR-flux profile data suggests that the microfiltration flux is controlled by the concentrated gel-laysr on the surface of the membrane, Table 3.

TABLE 3

| Microfiltration - VCR vs. Flux relationship | |
|---|---|
| VCR | Flux (liters/m²/hr) |
| 1.1 | 170.4 |
| 1.3 | 194.3 |
| 1.8 | 197.4 |
| 2.9 | 138.2 |
| 4.7 | 74.6 |
| 6.4 | 37.3 |
| 7.1 | 24.1 |
| 7.3 | 23.0 |
| 8.6 | 21.5 |
| 11.5 | 19.7 |

Example #3

Ultrafiltration

In this Example, a continuous three-stage GEA Filtration (Model U Pilot Plant) unit equipped with a Koch 3838 HFK328-VYT (5,000 NMWCO) ultrafiltration membrane per stage (5.4 m² each) was used to ultrafilter a PDO microfiltration permeate, for example, produced in Example #2. The ultrafiltration set up was fed at constant pressure, 60 psi and concentrated to 15-fold. Concentration was regulated by the flow control valve, positioned after the final membrane stage, and ratioed off of the inlet feed flow. The concentration ratio was maintained at 6.67% of the inlet feed flow to achieve the 15× retention. Using an inlet heat exchanger and three interstage coolers, the system temperature was controlled at 140° F. The transmembrane pressure across each element was maintained at 65 psi via a recirculating stage pump. Permeate flow was measured after each individual stage to determine flux and the permeate quality was determined with HPLC, GPC and Nitrogen Analysis (Antek). Table 4 demonstrates the operational performance of the individual filtration stages as well as the overall filtration. Table 5 shows the separation of PDO broth across the ultrafiltration membrane.

TABLE 4

Ultrafiltration operation

|   |   | Stage #1 | Stage #2 | Stage #3 | Total |
|---|---|---|---|---|---|
| intial | Concentration Factor | 1.49 | 2.94 | 15.83 | 15.83 |
|  | Flux (liters/m²/hr) | 38.96 | 38.96 | 32.74 | 36.9 |
| final | Concentration Factor | 1.52 | 3.16 | 16.10 | 16.1 |
|  | Flux (liters/m²/hr) | 22.80 | 22.80 | 17.41 | 21 |
| average | Concentration Factor | 1.56 | 3.27 | 15.08 | 15.08 |
|  | Flux (liters/m²/hr) | 29.01 | 27.35 | 21.14 | 25.8 |

TABLE 5

Separation characteristics

|  | Total Sugar Rejection (gram/L) | PDO (gram/L) | Nitrogen (ppm) | Ammonia (ppm) | Non-Ammonia Nitrogen (ppm) |
|---|---|---|---|---|---|
| Feed to Ultrafiltration | 8.7 | 107.9 | 993.0 | 1048.0 | 133.6 |
| Permeate | 8.1 | 116.4 | 817.1 | 951.0 | 37.3 |
| Retentate | 23.0 | 109.3 | 2729.9 | 1459.1 | 1533.4 |
| Rejection | 7% | 0% | 18% | 9% | 72% |

Multiple stages allows for better flux utilization at lower broth concentrations. As the PDO ultrafiltration feed concentrates through the system, the fluxes decline with an increasing concentration. Although the final concentrate leaving the skid is ~15-fold more concentrated than the original feed the overall flux performance is averaged over the three stages rather than being dictated by its lowest fluxing concentration. Ultrafiltration serves a prefiltration step to the nanofiltration. Protein is an irreversible foulant for the nanofiltration membranes, therefore with ultrafiltration removing 72% of the crude protein (protein and amino acids) the later downstream should operate with less restriction. Molecular weight analysis of the ultrafiltration retentate revealed that the retained protein(s) had an average molecular weight of approximately 12,000 Daltons and that its rejection by the membrane was complete. No other broth components are significantly rejected.

Example #4

Nanofiltration

In this Example, a continuous three stage GEA Filtration unit (Model U Pilot Plant) was used with three Koch TFC3838 SR3 (180 NMWCO) nanofiltration membranes, one per stage (4.8 m² each), was used to nanofilter a PDO ultrafiltration permeate, for example, of Example #3. The feed to the nanofiltration skid was maintained at constant, 200 psi and the system's concentration controlled at 20×. Retentate flow was ratioed, via the concentrate flow control valve ratioed to 5% of the inlet feed flow. Temperature was held constant at 120° F., with the use an inlet heat exchanger and three interstage coolers. The transmembrane pressure across each element was maintained at 205 psi via a recirculating stage pump. Permeate flow was measured after each individual stage to determine fluxes and the permeate quality was determined analytically with. HPLC, UV/Vis and IPC (Inductively Coupled Plasma Optical Emission Spectroscopy) techniques. Table 6 demonstrates the operational performance of the overall and individual filtration stages. Table 7 shows the separation of PDO broth across the nanofiltration membrane.

TABLE 6

Nanofiltration operation

|  | Stage #1 | Stage #2 | Stage #3 | Total |
|---|---|---|---|---|
| Concentration Factor | 1.72 | 4.3 | 20.2 | 20.2 |
| Flux (liters/m²/hr) | 68.1 | 56.8 | 30.3 | 51.7 |

TABLE 7

Nanofiltration separation characteristics

|  | Total Sugars (gram/L) | PDO (gram/L) | Divalent Cations (Ca + Mg) (ppm) | Monovalent Cations (Na + K) (ppm) | Sulfate Rejection (ppm) | Phosphate Rejection (ppm) | UV_270 nm |
|---|---|---|---|---|---|---|---|
| Feed to Nanofiltration | 7.31 | 111.84 | 31.03 | 247.62 | 150 | 650 | 2.875 |
| Permeate | 2.17 | 112.92 | 14.54 | 198.45 | 52 | 550 | 1.7628 |
| Retentate | 78.63 | 106.57 | 152.04 | 821.33 | 1480 | 2060 |  |
| Rejection | 70% | 0% | 53% | 20% | 65% | 15% | 39% |

The final concentrate exiting the nanofiltration was 20-fold more concentrated than the initial feed and the overall flux performance is an average of the individual stages. With the ultrafiltration pretreatment, the nanofiltration membranes demonstrated no fouling as the fluxes and concentration factors of the individual stages remained constant over the experiment.

In addition to the 90% reduction of visible color in the permeate stream, all of the major identified and uncharacterized impurities of the PDO process are removed through nanofiltration. Reduction in the sugars and the salts reduced ion exchange load and the decrease in UV has been shown to lessen the burden to distillation and improve final product quality.

Example #5

Ion Exchange

In this Example, a nanofiltration permeated PDO broth, for example, of Example #4 is batch processed through a cation-anion, cation-anion configured ion exchange. Each of the cation cells is comprised of a 1.5 ft diameter×8 ft high column loaded with 6 ft³ of Dowex 88 strong acid cation resin and each anion cell includes two 1.5 ft diameter×8 ft high columns and is loaded with 12 ft³ (6 ft³ per column) of Dowex®

77 weak base anion resin. The nanofiltered broth (34 meq/L) is fed to the ion exchange at 4.5 gpm at 115° F. with breakthrough occurring after 10 hours. Table 8 demonstrates the ion exchange operation and Table 9 depicts the general component profiles. The final process stream off of the ion exchange was analyzed by pH, conductivity, UV/Vis and refractive index while the product samples were analyzed with HPLC and IPC (Inductively Coupled Plasma Optical Emission Spectroscopy)

TABLE 8

Ion Exchange Operations

|  | UV_270 nm | Conductivity (uS/cm) | Dry Solids (%) | pH |
|---|---|---|---|---|
| Feed to Ion Exchange | 1.373 | 3400 | 90.0 | 7.59 |
| Process Sampling | 0.062 | 94.8 | 89.0 | 10.27 |
| Process Sampling | 0.074 | 88.5 | 89.3 | 9.72 |
| Process Sampling | 0.099 | 75.1 | 86.6 | 9.88 |
| Process Sampling | 0.120 | 68 | 90.3 | 9.78 |
| Process Sampling | 0.133 | 114.3 | 89.1 | 9.81 |
| Process Sampling | 0.131 | 256 | 88.1 | 10.25 |
| Process Sampling | 0.143 | 44.9 | 89.5 | 10.45 |
| Process Sampling | 0.170 | 36.2 | 87.4 |  |
| Process Sampling | 0.288 | 23 | 93.6 | 9.9 |
| Process Sampling | 1.047 | 21.4 | 94.8 | 9.4 |
| Composite Ion Exchange Product | 0.069 | 95.7 | 92.7 | 10.22 |

TABLE 9

Ion Exchange Component Profiles

|  | Organic Acids ppm (as_is) | Divalent Cations (Ca + Mg) ppm (as is) | Monovalent Cations (Na + K) ppm (as_is) | Chloride ppm (as_is) | Phosphate ppm (as_is) | Ammonia ppm (as_is) |
|---|---|---|---|---|---|---|
| Feed to Ion Exchange | 2826 | 8.05 | 176.5 | 55 | 405 | 702.3 |
| Ion Exchange Product | 38 | 4.25 | 27.38 | 2 | 2 | 2.3 |

Breakthrough occurs with the passage of product having conductivity greater than 250 uS/cm or a UV absorbance (at 270 nm) greater than 0.5 ABU. For this Example, breakthrough occurs as the result of the UV component eluting from the second set of anion columns. The ion exchange cells are sized sufficiently for ion removal as the overall ionic species are still 98% removed. Capacity of the ion exchange is dictated by the resins ability to absorb the UV contributor (s). Upon breakthrough, UV/Vis color and conductivity have been both reduced by greater than 95%. The removal of the UV components as well as the mineral species reduces the contaminants and foulants that are sent to the further downstream.

Example #6

Evaporation

The product stream leaving CACA ion exchange, for example, as in Example #5, comes off at 10-13% dry solids content and requires further concentration up to 80%. In this example, the ion exchange product is evaporated from 11% to 85% dry solid in a fed-batch evaporation. Feed is brought to the evaporator from an external feed tank and pumped into the recirculation loop of the evaporation unit. The recirculation loop feeds through a plate and frame heat exchanger, with 1000# steam/hr and then onto an elevated gas-liquid separator under 27 mm Hg vacuum and a 170° F. vapor temperature. The separator is elevated to provide sufficient head to displace the evaporated product back to the evaporator feed tank. The dry solids content of the material in the evaporator feed tank is recirculated through the evaporator until the target concentration is achieved. In situ sampling of the evaporated stream is performed through a calibrated refractive index measurement and later analysis is done with Karl Fischer moisture analysis and UV/Vis. Table 10 shows the PDO product analysis as the evaporation occurs. All of the UV/Vis analysis was done at a common 5% dry solids. Moistures were determined with Karl Fischer and then diluted to the reference concentration.

TABLE 10

Evaporation Results

|  | DS (%) | UV-270 nm |
|---|---|---|
|  | 25.22 | 0.224 |
|  | 29.12 | 0.230 |
|  | 38.33 | 0.234 |
|  | 59.86 | 0.245 |
|  | 82.91 | 0.214 |
| Composite | 85 | 0.264 |

The entire evaporation for this example took 16 hours to complete, over which period the product stream went from a water white to dark caramel color. The evaporation results indicated that no secondary reactions were occurring during the long residence evaporation and as a result, no additional UV or visible color was generated during the unit operation, only concentration of the initial feed stock.

Example #7

Mixed Ion Exchange

In this example, a mixed bed polishing is performed on an 83% dry solids evaporator product stream produced, for example, according to Example #6. Evaporation does not create additional color, but it does concentrate the residual color components that still require removal. The evaporated PDO product stream (200 gallons) was fed to a 40-60 mixture of strong acid cation exchange resin (Dowex 88) and strong base anion resin (Dowex 22) for the removal of residual salts and color. The mixed bed is a 1 ft diameter by 5 ft high column containing 6 ft³ of mixed bed resin that is fed at 1.5 gpm by a cooled (80° F.) evaporated 3 G stream. Table 11 and 12 demonstrate the mixed bed's polishing capacity.

TABLE 11

Mixed Bed Polishing Color Removal

| | Absorbance (nm) | | | | | |
|---|---|---|---|---|---|---|
| | 210 | 230 | 250 | 270 | 290 | 310 |
| Mixed Bed Feed | 2.529 | 1.810 | 1.063 | 0.957 | 0.587 | 0.296 |
| Composite Mixed Bed Product | 1.634 | 1.191 | 0.457 | 0.373 | 0.231 | 0.085 |

TABLE 12

Mixed Bed Polishing Ion Exchange

| | Conductivity (uS/cm) | pH |
|---|---|---|
| Mixed Bed Feed | 23.7 | 7.73 |
| Composite Mixed Bed Product | 0 | 8.38 |

Like the CACA ion exchange, the mixed bed has the capacity to absorb the color components of the evaporated product stream. Visible color is drastically improved from a deep caramel color to a near water white solution, while the UV contributors are also significantly removed. The ion exchange capacity of the column is well in excess of the ion load of the feed, hence the product leaving the mixed bed has no measurable conductivity and there is a slight basic shift in the product's pH.

Example #8

Hydrogenation

The primary purpose of chemical reduction is to reduce the color in polymers made from bio-PDO, specifically in PDO polymers. Polymer color is determined by L*a*b* measures. A polymer with a b*<1 is considered to have an acceptable color for most polymer applications. A criterion was developed to relate the quality of PDO to the color of the polymer. The UV absorption at 270 nm was identified to be a reasonable indicator of the PDO quality and the color of the final polymer. The UV spectra are normally collected at a 1:5 dilution ratio and reported as diluted numbers. It is believed that a color metric of 270 nm UV below 0.1 will result in acceptable PDO polymer quality.

The color in PDO appears related to the composition of the feed to refining and treatment conditions in the refining process. Feed to refining contains water, glycerol and other heavies (such as sugars). The following Table 13 shows the sugar composition of a representative evaporated broth. While the current separation scheme, including the nanofiltration step, removes a significant amount of these sugars, some of the sugars can remain in the broth and enter into the refining train.

These sugars are believed to cause color formation during heat treatment. It has been observed, in heat treatment of a "chemically produced" Wesseling PDO doped with 1% maltose in a nitrogen environment, that the color level in the product is low at temperatures below 130° C. Above 150° C., however, broad bands are observed in the UV around 230 nm and between 270 and 290 nm as well. Most of these color compounds distill before or with PDO. An increase in color is accompanied by a concomitant decrease in the pH of the treated product.

The distillation refining process of the invention requires thermal treatment. A four distillation column process is preferred. Column 1 is aimed primarily at the reduction of water, which is removed in the overhead. Column 2 separates the heavy components like glycerol and sugars from the PDO. Columns 3 and 4 remove the residual light and heavy compounds and produce a product having the required properties. Applicants believe that color formers are due to aldehydes, ketones, and furan derivatives. This belief has led to the evaluation of several technologies for reducing color. Over ten different techniques were tested. Adsorption on carbon and hydrogenation were the most promising alternatives. All the other techniques were partially effective—they initially reduced the color, but upon further processing generated more undesirable impurities.

Generally, the materials and methods for hydrogenation are well-known in the art. In the Example that follows, shaker-tube, autoclave and up-flow fixed bed tubular reactors were used, which operated in batch, semi-batch and flow modes using fine powder, granular and extrudate catalysts.

The PDO color quality was measured by a UV/Vis spectrophotometer. All the UV analyses were done using a HP 8453 UV/Vis spectrophotometer at 20% dilution with water and reported as such. The impurities in PDO were measured with gas chromatography. All GC analyses were done with an Agilent 6890 Gas Chromatograph using a 7673 series autoinjector, 5973N Mass Selective Detector, HP-INNOWax polyethyleneglycol capillary column, 30 m long, 250 micrometer diameter, 0.25 micrometer film thickness. The initial temperature is 100° C., which increased at 10° C./min rate to 193° C., followed by an increase in temperature to 250° C. at 40° C./min and held for 12 min.

The sulfur was analyzed by a Perkin-Elmer 3300RL Inductively Coupled Plasma (ICP) analyzer. The acidity of polyol was analyzed with a Beckman Model 350 pH meter. The pH is measured in two ways: neat and in 50/50 dilution with water.

General Protocol

A previously purified 1,3-propanediol (PDO) was used as the starting material. The PDO had been prepared in a fermentation process starting from dextrose and purified in various steps including, but not limited to microfiltration, nanofiltration, ion exchange, evaporation, spray-drying, carbon

TABLE 13

Unfermented sugars in light evaporated fermentation broth
Carbohydrates by HPAE-PAD

| Sample ID | Description | Iso-highers (DP2-DP12) | Isomaltose | Panose | Ug/ml Maltose | Maltotriose | Maltotetraose | Dextrose | Fructose |
|---|---|---|---|---|---|---|---|---|---|
| 73061 | Light evap product | 6650 | 6470 | 4880 | 1050 | 500 | 250 | 145 | 110 |
| 73329 | Light evap product | 6160 | 6340 | 4410 | 1010 | 505 | 190 | 240 | 140 | adsorption, chromatographic separation, and various stages of distillation. Depending on the elements of the fermentation process and the particular purification steps used in each case, the crude PDO solution used in the following examples contained various impurities. Each set of Examples uses a PDO made via a different combination of fermentation and/or pre-cleaning processes and are designated as Cases A, B, and C.

Case A: Use of Hydrogenation Step after Four-Step Distillation of Aqueous Mixture.

In this series of Examples (8)(1-9), a PDO solution purified in various steps of filtration, adsorption, ion-exchange and evaporation followed by four stages of distillation was used as the feed to hydrogenation. GC analysis of this feed showed over 22 unknown impurities, comprising over 0.13% of the area counts. The UV/Vis spectrum of the crude feed had three wide absorption bands with maxima around 200, 220, and 270-280 nm.

Examples #(8)1-(8)8

In these examples, PDO described in Case A was hydrogenated in a shaker tube with RANEY 2400 Nickel slurry catalyst (Cr and Fe promoted Ni) at the various operating conditions summarized in Table 1. In all cases 200 g of PDO was placed in a 400 mL stainless steel shaker tube with the proper amount of the catalyst. The shaker tube was purged with nitrogen, heated to the specified temperature, and pressurized with hydrogen to the designated pressure. The reactor was kept shaking for the specified time, then cooled and depressurized. The quality of the hydrogenated product was determined with GC and UV/VIS as described above. Table 14 shows the reduction in the UV absorption at 280 nm.

TABLE 14

Conditions and results of Examples 8(1)-8(8)

| Example# | Temp. C. | Pressure Psia | Cat. Wt % | Time hr. | UV-280 A.U. |
|---|---|---|---|---|---|
| Feed |  |  |  |  | 1.58 |
| 1 | 80 | 400 | 0.05 | 1 | 0.64 |
| 2 | 100 | 400 | 0.05 | 1 | 0.65 |
| 3 | 80 | 800 | 0.05 | 1 | 0.99 |
| 4 | 100 | 800 | 0.05 | 2 | 0.46 |
| 5 | 100 | 100 | 0.125 | 0.25 | 1.28 |
| 6 | 100 | 100 | 0.125 | 1 | 1.08 |
| 7 | 120 | 400 | 0.125 | 1 | 0.53 |
| 8 | 140 | 400 | 0.125 | 1 | 0.42 |

Color removal improves with temperature, contact time and amount of catalyst. In Example (8)1, hydrogenation completely eliminated nine of the twenty-two impurities in crude PDO solution and reduced the concentration of five, formed six new compounds, and increased the concentration of three existing impurities. The formed impurities were either much lighter or much heavier than PDO, and therefore could be easily removed by distillation. These compounds with their designated retention times are shown in Table 15. In Examples 8(2) to 8(8), similar changes in the impurities were observed, though not to the same extent, depending on the severity of the operating conditions.

TABLE 15

Changes in the Impurities of PDO upon Hydrogenation
Example (8)1: Composition Change in Hydrogenation

| Retention Time | Change |
|---|---|
| 1.282 | disappeared |
| 1.306 | Formed |
| 1.439 | Formed |
| 2.246 | disappeared |
| 3.253 | disappeared |
| 4.191 | disappeared |
| 4.270 | Formed |
| 5.285 | disappeared |
| 5.674 | unchanged |
| 5.760 | Increased |
| 5.902 | Reduced |
| 6.104 | unchanged |
| 6.900 | unchanged |
| 7.333 | unchanged |
| 7.490 | Formed |
| 8.058 | disappeared |
| 8.567 | disappeared |
| 8.828 | disappeared |
| 9.206 | unchanged |
| 9.278 | unchanged |
| 9.616 | Formed |
| 9.743 | Reduced |
| 9.847 | unchanged |
| 10.257 | Increased |
| 10.386 | unchanged |
| 10.620 | Formed |
| 10.669 | Reduced |
| 10.827 | Increased |
| 11.395 | disappeared |

Example #(8)9

Following the shaker tube tests of Examples (8)1-(8)8, 11.8 kg of the PDO solution from Example 8(1) was charged in a 5 gal autoclave reactor with 24 g of RANEY 2400 Nickel slurry catalyst. The mixture was hydrogenated at 400 psig and 120° C. for 4 h. The process was repeated three times and the products were combined and distilled in two pilot scale distillation columns to remove the lights and heavies. The final product had a UV-270 below 0.3 AU. This purified PDO was polymerized to form poly-trimethylene-terephthalate that was clearly colorless with a b-color of 0.33. The PDO without this hydrogenation and distillation process produced a polymer with a b-color over 1.2. The pH of the PDO before hydrogenation was 4.6; after hydrogenation the pH improved to 6.8.

Case B. Use of Invention on Crude 1,3-Propanediol (Before Distillation)

As a process simplification, a more crude 1,3-propanediol was used in a second series of tests. This 1,3-propanediol was also prepared in the fermentation process described above, starting from dextrose and purified in various steps of filtration, ion exchange, and evaporation but was distilled in only two distillation columns instead of four. GC analysis of this feed showed over 40 unknown impurities, comprising about 1% of the area counts. The UV/Vis absorption was quite strong, such that after diluting to 20%, its UV-270 absorption was 3.4 AU.

Example #(8)10

12.5 kg of the crude PDO solution described in Case B above, was charged in a 5 gal autoclave reactor with 52 g of RANEY Nickel slurry catalyst. The mixture was hydrogenated at 400 psig for one h at 120° C. followed by 4 h at 130° C. Three additional batches were similarly hydrogenated and the products were combined and distilled in two pilot scale distillation columns to remove the lights and heavies. The final product had a UV-270 below 0.1 AU. This purified 1,3-propanediol was polymerized to form clearly colorless poly-trimethylene-terephthalate with a b-color of 0.88. The pH of the PDO before hydrogenation was 4.7; after hydrogenation the pH improved to 6.6.

Case C. Use of Invention on 1,3-Propanediol, with Modified and Improved Pre-Purification By changes in the fermentation and purification process conditions, several crude PDO solutions with improved quality were obtained. These PDO solutions were hydrogenated in an up-flow, packed bed reactor under various conditions. The reactor was a ¾ in. diameter and 20 in. long stainless steel-jacketed reactor. Hot oil flowing in the jacket maintained a constant temperature in the reactor. The reactor was packed with desired lengths of catalyst supported between two layers of inert packing. PDO and hydrogen entered into the reactor from the bottom at the desired pressure. They passed through the reactor in an upflow mode, separating in a separator downstream of the reactor. Various catalysts were tested including a commercial granular RANEY nickel (Cr and Fe promoted Ni) and a commercial nickel on silica/alumina catalyst containing 50-60% Ni, using a nickel catalyst supported on alumina/silica.

Examples #(8)11(8)20

In these examples, a PDO described as Case C was hydrogenated with three commercial catalysts at various operating conditions. The operating conditions of each example and the results are shown in Table 16. Color removal improves with temperature and increased contact time or reduced space velocity. Pressure has minimal effect on color removal. Sulfur is completely removed in all cases where it was measured and pH of the product improved from an acidic to a more neutral range.

TABLE 16

| Example | Catalyst | LHSV, 1/h | $H_2$/PDO, scc/g | Temp. °C. | Press. psig | Product UV | S ppm | pH |
|---|---|---|---|---|---|---|---|---|
| Feed |  |  |  |  |  | 1.52 | 13 | 5.7 |
| 11 | RANEY Ni | 4 | 21.3 | 120 | 400 | 0.35 |  |  |
| 12 | RANEY Ni | 4 | 21.3 | 120 | 650 | 0.32 |  |  |
| 13 | Ru/C | 4 | 21.3 | 120 | 400 | 0.33 |  |  |
| 14 | Ni/SiO$_2$—Al$_2$O$_3$ | 4 | 21.3 | 80 | 400 | 0.55 |  |  |
| 15 | Ni/SiO$_2$—Al$_2$O$_3$ | 4 | 21.3 | 100 | 400 | 0.47 |  |  |
| 16 | Ni/SiO$_2$—Al$_2$O$_3$ | 4 | 21.3 | 60 | 400 | 0.74 |  |  |
| 17 | Ni/SiO$_2$—Al$_2$O$_3$ | 4 | 21.3 | 40 | 400 | 0.87 |  |  |
| 18 | Ni/SiO$_2$—Al$_2$O$_3$ | 3.8 | 22.4 | 120 | 400 | 0.32 |  |  |
| 19 | Ni/SiO$_2$—Al$_2$O$_3$ | 1.9 | 22.4 | 120 | 400 | 0.35 | 0 | 7.5 |
| 20 | Ni/SiO$_2$—Al$_2$O$_3$ | 1.27 | 22.4 | 120 | 400 | 0.15 | 0 | 6.7 |

Example #9

Purity Characterizations

In the chart below, biologically-produced 1,3-propanediol purified by the process of the invention is compared, in several purity aspects, to two separate, commercially-obtained preparations of chemically-produced 1,3-propanediol.

TABLE 17

|  | Units | Source A | Source B | Bio-PDO |
|---|---|---|---|---|
| Total Organic Impurities Bio - PDO | Ppm | 570 | 695 | 80 |
| UV Abs 220 nm, | AU | 0.25 | 1.15 | 0.12 |
| UV Abs 250 nm, | AU | 0.123 | 0.427 | 0.017 |
| UV Abs 275 nm | AU | 0.068 | 0.151 | 0.036 |
| UV Abs 350 nm | AU | 0.013 | 0.007 | 0.001 |
| Peroxides | ppm | 67 | 43 | 2 |
| CIE L*a*b* ASTM D6290 | b* | .411 | .03 | .1 |
| Carbonyls | ppm | 147 | 175 | 1 |

A typical profile of purity aspects is provided below for a sample of biologically-produced 1,3-propanediol purified by the process of the invention.

TABLE 18

|  | Units |  |
|---|---|---|
| 1,3-Propanediol | GC area % | 99.992 |
| pH, neat | pH | 8.22 |
| UV Abs. @ 270 nm, 1:5 dilution | AU | 0.01 |
| Color APHA |  | 3 |
| Color (Process Measurement) L*a*b* | b* | 0.10 |
| Water | ppm | 115 |
| UV abs 220 nm neat | AU | 0.144 |
| UV abs 250 nm neat | AU | 0.017 |
| UV abs 275 nm neat | AU | 0.036 |
| UV abs 350 nm neat | AU | 0.001 |
| Peroxide | ppm | 2 |
| Metals | ppm | <1 |
| Sulfur | ppm | <1 |
| Carbonyl | Ppm | 1 |

The unit ppm of total organic impurities means parts per million of total organic compounds in the final preparation, other than 1,3-propanediol, as measured by a gas chromatograph with a flame ionization detector. Results are reported by peak area. A flame ionization detector is insensitive to water, so the total impurity is the sum of all non-1,3-propanediol organic peaks (area %) ratioed to the sum of all area % (1,3-propanediol included). The terms "organic materials" or "organic impurities" refer to the contaminants containing carbon.

What is claimed is:

1. A process of purifying biologically-produced 1,3-propanediol from the fermentation broth of an organism able to produce 1,3-propanediol, comprising the steps of:

(a) subjecting the fermentation broth to filtration;
(b) subjecting the product of step (a) to ion exchange purification wherein anionic and cationic molecules are removed;
(c) subjecting the product of step (b) to chemical reduction; and
(d) subjecting the product of step (c) to a distillation procedure comprising at least two distillation columns wherein one of said distillation columns removes molecules having a boiling point exceeding the boiling point of 1,3-propanediol and the other of the distillation columns removes molecules having a boiling point below the boiling point of 1,3-propanediol.

2. The process of claim 1, wherein said chemical reduction is selected from the group consisting of hydrogenation and hydroboration.

3. The process of claim 2, wherein said chemical reduction is hydrogenation.

4. The process of claim 1, further comprising wherein the fermentation broth is subjected to an evaporation step.

5. The process of claim 4, wherein said evaporation step is conducted during step (b).

6. The process of claim 1, wherein the filtration process of step (a) comprises more than one separate filtration procedure.

7. The process of claim 6, wherein the filtration process of step (a) comprises a first and a second filtration procedure, said first filtration procedure comprising subjecting the fermentation broth to microfiltration comprising removing molecules having a size greater than 0.2 microns and said second filtration procedure comprising removing molecules having a molecular weight greater than about 200 Daltons.

8. The process of claim 6, wherein the filtration process of step (a) comprises a first, a second and a third filtration procedure: said first filtration procedure comprising subjecting the fermentation broth to microfiltration comprising removing molecules having a size greater than 0.2 microns; said second filtration procedure comprising subjecting the fermentation broth to ultrafiltration comprising removing molecules having a molecular weight greater than about 5000 Daltons, and said third filtration procedure comprising subjecting the fermentation broth to nanofiltration comprising removing molecules having a molecular weight greater than about 200 to 400 Daltons.

9. The process of claim 1, wherein the ion exchange process of step (b) comprises more than one separate ion exchange procedure.

10. The process of claim 9, wherein the ion exchange process of step (b) comprises subjecting the product of step (a) to one or more series of ion exchange procedures wherein each series of procedures comprises exposing the product to a strong acid cation exchange resin followed by exposure to a weak base anion exchange resin.

11. The process of claim 9, wherein the ion exchange process of step (b) comprises subjecting the product of step (a) to two series of ion exchange procedures wherein each series comprises exposing the product to a strong acid cation exchange resin followed by exposing the product to a weak base anion exchange resin.

12. The process of claim 11, wherein the ion exchange process of step (b) further comprises subjecting the product to a mixed ion exchange resin composition comprising a mixture of strong acid cation exchange resin and strong base anion exchange resin.

13. The process of claim of 1, wherein step (b) comprises subjecting the product of step (a) to two series of ion exchange procedures wherein each series comprises exposing the product to a strong acid cation exchange resin followed by exposing the product to a weak base anion exchange resin; followed by an evaporation step; followed by subjecting the product to a mixed ion exchange resin composition comprising a mixture of strong acid cation exchange resin and strong base anion exchange resin.

\* \* \* \* \*